United States Patent [19]

Ferek-Petric et al.

[11] Patent Number: 5,799,350
[45] Date of Patent: Sep. 1, 1998

[54] BLOOD FLOW VELOCITY MEASUREMENT DEVICE

[75] Inventors: Bozidar Ferek-Petric; Branko Breyer, both of Zagreb, Croatia

[73] Assignee: Pacesetter AB, Solna, Sweden

[21] Appl. No.: 718,406

[22] PCT Filed: Mar. 29, 1995

[86] PCT No.: PCT/EP95/01171

§ 371 Date: Feb. 27, 1997

§ 102(e) Date: Feb. 27, 1997

[87] PCT Pub. No.: WO95/26677

PCT Pub. Date: Oct. 12, 1995

[30] Foreign Application Priority Data

| Mar. 30, 1994 | [HR] | Croatia | 940206 A |
| May 16, 1994 | [HR] | Croatia | 940303 A |
| Aug. 1, 1994 | [HR] | Croatia | 940034 A |

[51] Int. Cl.⁶ ............... A61N 1/365
[52] U.S. Cl. ............... 607/17
[58] Field of Search ............... 600/465, 466, 600/467; 607/6, 9, 17, 19

[56] References Cited

U.S. PATENT DOCUMENTS

| 5,174,289 | 12/1992 | Cohen | 607/9 |
| 5,243,976 | 9/1993 | Ferek-Petric et al. | 607/19 |
| 5,318,595 | 6/1994 | Ferek-Petric et al. | 607/17 |

*Primary Examiner*—Scott M. Getzow
*Attorney, Agent, or Firm*—Hill & Simpson

[57] ABSTRACT

An intracardiac blood flow velocity measurement device has a catheter adapted to be inserted through a blood vessel into the heart, at least two electrodes made of two different biocompatible materials mounted on the catheter at a detecting position which is located in a selected detecting area when the catheter is inserted into the heart for detecting blood flow velocity, with at least one of the electrodes being formed as a polarizable electrode and being disposed in the detecting position, and another of the electrodes being located on the catheter at an axially spaced distance from the polarizable electrode. Variation in an over-voltage or in a galvanic voltage is detected, and is used as a blood flow velocity signal.

22 Claims, 7 Drawing Sheets

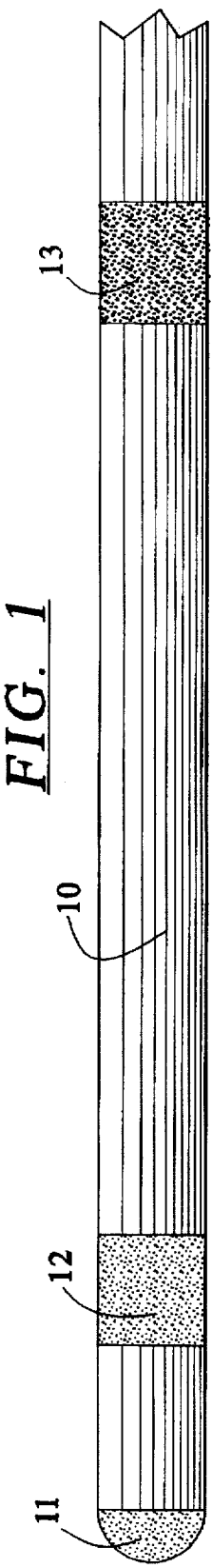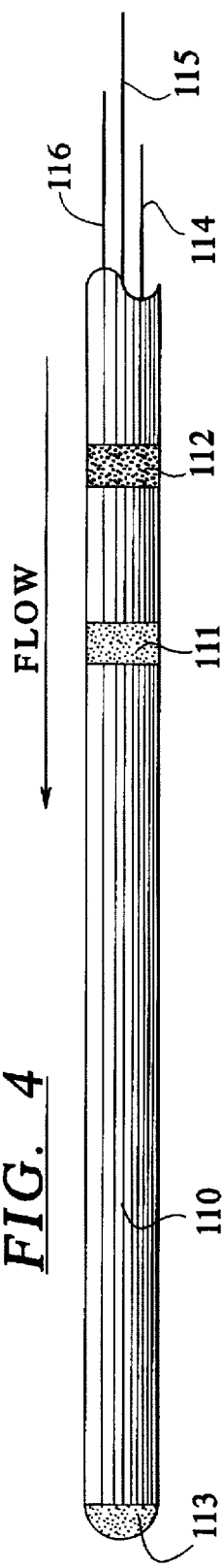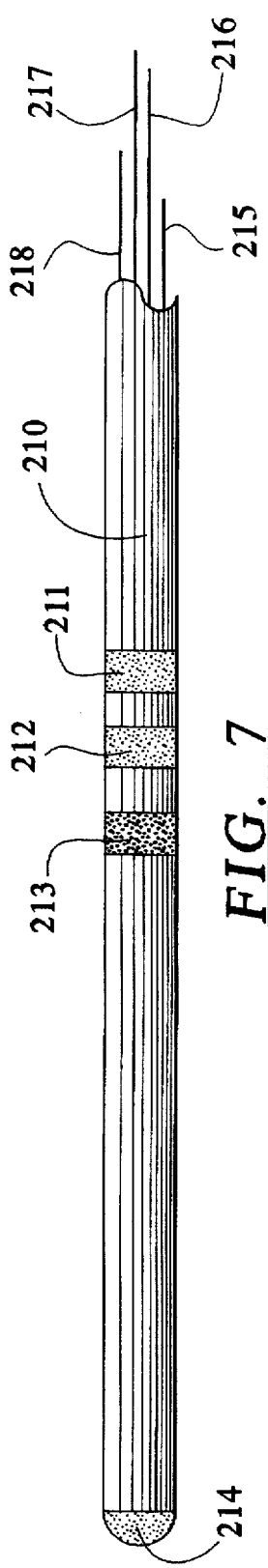

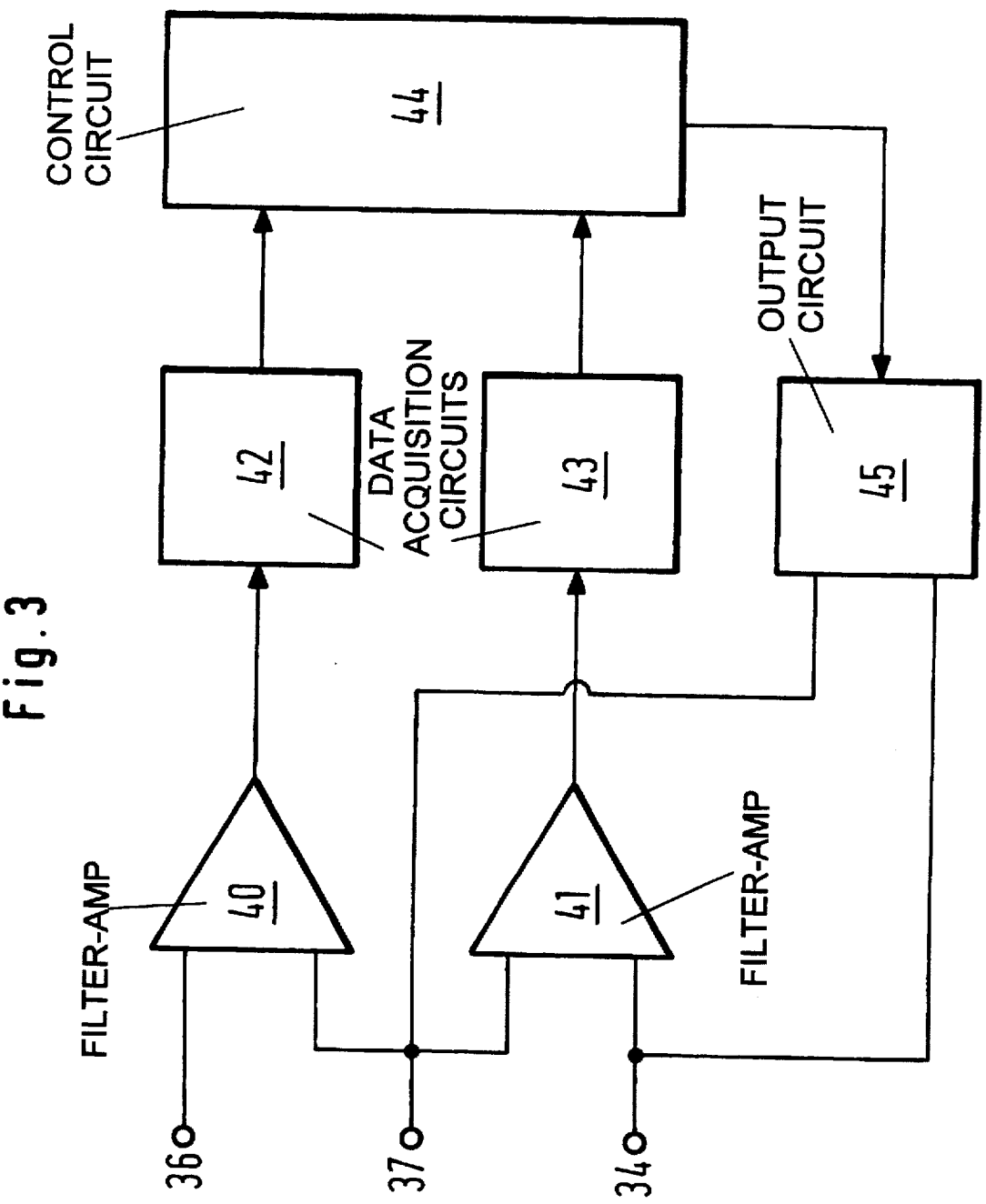

BLOOD FLOW VELOCITY MEASUREMENT DEVICE

FIELD OF THE INVENTION

This invention relates to a blood flow velocity measurement device. Such a device is used for the measurement of blood flow velocity characteristics within the heart and large blood vessels especially for the purpose of control of the electrotherapy.

BACKGROUND OF THE INVENTION

Physiologic cardiac pacing is very important on temporary as well on permanent basis Temporary pacing is usually applied either after cardiac surgery or during myocardial infarction because of the transient conduction disturbance or arrhythmia. Patients in rest have significantly improved cardiac output when ventricular contraction is synchronous with atrial filling of ventricles. This is very important for faster recovery after surgery or after myocardial infarction. Furthermore, some arrhythmias like supraventricular tachycardias and extrasystolies may be prevented by means of physiologic pacing.

Patients with chronic conduction and rhythm disturbance have to receive a permanent implantable pacing system. They also have a significant contribution of atria to the hemodynamic benefit. There are two basic modes of physiologic cardiac pacing: sequential and synchronous. The sequential atrio-ventricular pacing is used to restore normal atrio-ventricular physiologic sequence. In this mode, an atrium and a ventricle are paced by twin stimuli separated by an appropriate physiologic interval. However the heart rate is controlled by the pacemaker program and does not vary according to the physiological nexus. The synchronous cardiac pacing approximates most closely to the normal cardiac rhythm. The spontaneous atrial electrogram (P-wave) is sensed by an electrode usually in contact with the atrial endocardium and this is used to trigger the ventricle after an appropriate preset delay. Because the atrial rhythm is paced by our natural pacemaker sinus-atrial node, the frequency varies naturally according to the body workload. Therefore the P-wave synchronous ventricular cardiac pacing is considered to be the most physiologic rate-responsive pacing. p Accordingly, our invention disclosed in U.S. Pat. No. 5,243,976 and in U.S. Pat. No. 5,316,001 enables new method of physiologic cardiac pacing. The aim of our invention is to provide a pacemaker which will, in normal atrial rhythm, act in a synchronous mode (VDD) and maintain atrio-ventricular synchronism, yet with the need for implantation of a single lead. In carrying out the invention, the blood flow within the heart is monitored with a device for the blood flow velocity measurement mounted on a cardiac pacing lead. Particularly the flow waveform through the tricuspid valve is used for synchronization and control of ventricular cardiac pacing. The early rapid diastolic filling wave (E-wave) as well as the late atrial diastolic filling wave (A-wave) are detected and their parameters are measured. The ventricular pacing is synchronized with the A-wave. The device provides sensors for rate responsive ventricular pacing and reliable means for atrial fibrillation detection. It is another object to provide continuous monitoring of the right ventricular filling dynamics in order to estimate the ventricular muscle performance and to automatically reprogram the maximum tracking rate in such a way as to prevent the angina pectoris and the high-rate induced myocardial ischemia. Our system is capable to detect single premature ventricular contractions, as well as it is capable to discriminate the sinus tachycardia from the pathologic tachycardia. It provides confirmation of the ventricular capture and detection of right ventricular failure.

Another system, disclosed in our U.S. Pat. No. 5,318,595 monitors the ventricular filling and actually regulates the pattern of ventricular filling waveform by means of the A-V interval adjustment for the purpose of hemodynamics optimisation.

It is very important for proper function of these inventions to utilise the low power, long term reliable and accurate method of blood flow measurement, suitable for implementation in implantable devices. European Application 0 311 019 describes a system controlled by measurement of the impedance of the right ventricular cavity. While described system operates on a single lead it is essentially different to our invention. Measurement of the impedance actually acquires data about the ventricular volume change. The main advantage of our invention is that we infer the blood flow directly by measurement of the actual flow characteristics. It is very well known in the art that the atrial contraction contributes very little to the ventricular volume change. In contrary to that, atrial contraction produces a significant percentage of transvalvular flow. In our invention the waveform comprises easy discernable blood flow velocity waves which occur in ventricular diastole in physiologically prescribed order. Therefore our method is more sensitive and specific and, moreover, various measurements are possible in our invention for purpose of rate responsive pacing and arrhythmia detection.

European Application 0 347 708 describes a system controlled by measurement of the right heart pressure and estimated right heart volume. According to the cardiac physiology, right atrial pressure and volume, right ventricular pressure and volume are mutually related by means of the specific pressure-volume functions describing the cardiac muscle performance. The flow waveform through the tricuspid valve is obviously related to the function of right atrium as well as of right ventricle. The particular property of our invention is that the atrial as well as the ventricular function is monitored by means of the measurement of only one physiologic parameter—transvalvular blood flow velocity. Therefore our invention uses only one sensor preferable in a position nearby the tricuspid valve i.e. in the atrium.

U.S. Pat. No. 4,600,017 discloses the pressure measurement method by means of a piezoelectric sensor fixed on the cardiac pacing lead. Our sensor assembly for blood flow measurement is very specific and not identical to a simple pressure bimorph sensor. There is no doubt that in our invention, diastolic blood flow waveform measured through the tricuspid valve clearly demonstrate opening and closing of the tricuspid valve. However, in our invention, the timing of the valve motion, whether opening or closing, is not important for any kind of cardiac electrotherapy control.

U.S. Pat. No. 5,139,020 describes the system which monitors the systolic function of the heart. As disclosed therein, the ultrasonic beam is directed towards the left ventricle or aortic root because preferred embodiment of invention measures blood flow in aorta by means of a Doppler system. Another embodiment measures systolic time intervals in order to estimate myocardial contractility. However, there is a need for a method of blood flow velocity measurement consuming low power, which will be convenient to be utilized in implantable pacemaker but not impeding the pacemaker longevity.

U.S. Pat. No. 3,930,493 discloses an intracardiac blood flow velocity measurement device in accordance with the preamble of claim 1. In case of this device a polarographic cathode of e.g. gold or platinum and a reference anode of for instance silver/silverchloride or aluminium are attached on a catheter body for measuring the flow rate of blood within the cardiovascular system of a human body. The basis for flow rate measurement by the use of a polarographic cathode-anode is the provision of conditions by which the supply of oxygen to the cathode is made dependant upon the linear flow rate rather than upon an oxygen diffusion and for this purpose an appropriate sensing voltage (typically 0.4 to 0.9 volts) is applied to the electrodes. The current measured between the sensing cathode-anode pair indicates the flow rate. In case of the intravascular liquid velocity sensing method disclosed in U.S. Pat. No. 3,930,493 an external energy source is necessary for blood flow velocity measurement.

It is well known from the prior art (R. Plonsey & D. G. Fleming: "Bioelectric Phenomena", McGraw-Hill Series in Bioengineering, New York 1969, Chapter 2.) that the metal electrode immersed within the ionic liquid media produces a half-cell potential. Two different electrodes form a galvanic cell wherein positive electrode is called to be an anode and the negative electrode is a cathode. These electrochemical phenomena are pertinently studied and disclosed in numerous prior art references.

The standard half-cell potential of an electrode is defined when no electrical current exists between the electrode and the electrolyte. If there is a current, the measured half-potential is altered due to the polarization of the electrode. Theoretically, two kinds of electrodes exist: those that are perfectly polarizable and those that are perfectly nonpolarizable. Polarizable electrodes are those in which no actual charge crosses the electrode-electrolyte interface when a current is applied. This current is actually a displacement current because a polarizable electrode behaves as if it were a capacitor. Non-polarizable electrodes are those in which current passes freely across the electrode electrolyte interface. Some practical electrodes acquire very close these characteristics. Accordingly, the electrodes made of noble metal are relatively inert and it is very difficult for them to oxidize and dissolve. Such an electrode produces a strong capacitive effect, thus being almost an ideal polarizable electrode. The difference in potential between the measured half-cell potential and the equilibrium zero-current half-potential is known as the overvoltage. There are three electrochemical phenomena which contribute to development of overvoltage and consequently it is a superimposition of its three components: the ohmic overvoltage, the concentration overvoltage and the activation overvoltage. The ohmic overvoltage appears due to the resistance of the electrolyte. There is a voltage drop between two electrodes along a current path within the electrolyte. The voltage drop is proportional to the current and the resistivity of the electrolyte. However, the ohmic overvoltage is not linearly related to the current and therefore this phenomenon does not follow Ohm's law.

The variation of distribution of ions at the metal-electrolyte interface causes the concentration overvoltage. In equilibrium, when no current flows between the electrode and the electrolyte, the rates of oxidation and reduction at the interface are equal. When a current is established, or electrode is moved within the electrolyte, or the electrolyte flow appears, the equality is no longer true. Accordingly, the concentration of ions change and the difference in half potential occurs caused by the concentration overvoltage.

The oxidation of metal atoms into ions is possible if an atom is capable to break the energy barrier—activation energy. The reduction of electrolyte cations into metal atoms also includes the activation energy. When the current flows between electrode and the electrolyte, either reaction is predominant and the two activation energies for oxidation and reduction respectively, are different. This energy difference yields as a voltage difference—activation overvoltage.

The net overvoltage is an addition of all these three overvoltages. Nevertheless, the overvoltage in electrodes made of noble metal is predominantly a result of the concentration overvoltage. The overvoltage phenomena have been pertinently studied and described in numerous prior art references. This is due to the fact that the main goal of the design of biopotential recording electrodes for various applications is to minimize the overvoltage and distortion of recorded biopotential signal caused by the overvoltage. In contrary to that, the overvoltage phenomenon is used in this invention. The electrolyte flow changes the distribution of ion in the vicinity of the electrode-electrolyte interface thus changing the concentration overvoltage. This is the rationale to utilize the polarizable electrode as a flow velocity sensor.

SUMMARY OF THE INVENTION

It is an object of this invention to provide a device for blood flow measurement which will be convenient to be utilized in an implantable pacemaker and which consumes low power and therefore ensures increased longevity. It is a further object to provide a pacemaker which needs one electrode for detecting the mechanical activity of the atrium or of the ventricle of the heart.

The above object is achieved in accordance with the principles of the present invention in an intracardiac blood flow velocity measurement device, having a catheter adapted to be inserted through a blood vessel into the heart, at least one detecting device which detects the blood flow velocity, mounted on the catheter at a detecting position which comes to be located in the desired detecting area when the catheter is inserted into the heart, electrical conductors contained in the catheter connected at their distal ends to the detecting device and connected at their proximal ends to electronic circuitry for receiving and processing the blood flow velocity data detected in the detecting area, and the detecting device being formed by at least two electrodes of respectively different biocompatible materials, with at least one of the electrodes being a polarizable electrode and being arranged in the detecting position and the other of the electrodes being located axially spaced from the polarizable electrode along the catheter.

The device according to the invention is able to measure the blood flow velocity within the heart, particularly the flow through the tricuspid valve. The blood flow signal is used for cardiac electrotherapy synchronization and control. The bipolar cardiac pacing lead comprises an additional electrode, being the third electrode affixed to the lead, within the flow measurement volume i.e. in the vicinity of the tricuspid valve. This electrode can be made of some noble metal in order to have the properties of the polarizable electrode. The voltage is measured between this polarizable electrode and a proximal indifferent pacing electrode. The blood flow causes the change of the concentration overvoltage due to the fact that the ion distribution in the blood in the vicinity of the electrode is modulated by the flow velocity. Signal processing of the polarizable electrode overvoltage is done for the purpose of monitoring and/or of cardiac pacing control. In another embodiment of this invention, the cardiac electrotherapy system additionally comprises the electrodes forming a galvanic cell in the vicinity of tricuspid valve. The blood flow changes the ion concentration and therefore changes also the galvanic potential. Variation of the galvanic potential is detected within the electrotherapy device for the purpose of electrotherapy control. In a third embodiment, the cardiac pacing lead comprises three additional and equal electrodes mounted adjacently and equidistantly to each other within the flow measurement volume. First two adjacent electrodes of three electrodes are only bipolar intracardiac electrogram sensing electrodes, while the second two adjacent electrodes of three electrodes constitute the galvanic cell and also bipolar sensing electrode. When the signal of first two electrodes is subtracted from the signal of the second two electrodes only the flow signal is measured from the second electrodes.

DESCRIPTION OF THE DRAWINGS

FIG. 1 is a side view of a distal end of a lead having an electrode which will form a polarizable electrode in ionic fluid, when implanted, and having bipolar pacing/sensing electrodes, constructed in accordance with the principles of the present invention.

FIG. 3 is a block circuit diagram of VDD pacemaker, for use with the lead shown in FIG. 1, as well as with the other embodiments of the lead in accordance with the invention.

FIG. 4 is a side view of the distal end of a lead having electrodes which will form a galvanic cell in ionic liquid, when implanted, constructed in accordance with the principles of the present invention.

FIG. 7 is a side view of the distal end of a lead having three electrodes for flow measurement, constructed in accordance with the principles of the present invention.

DESCRIPTION OF THE PREFERRED EMBODIMENTS

Figure 2:
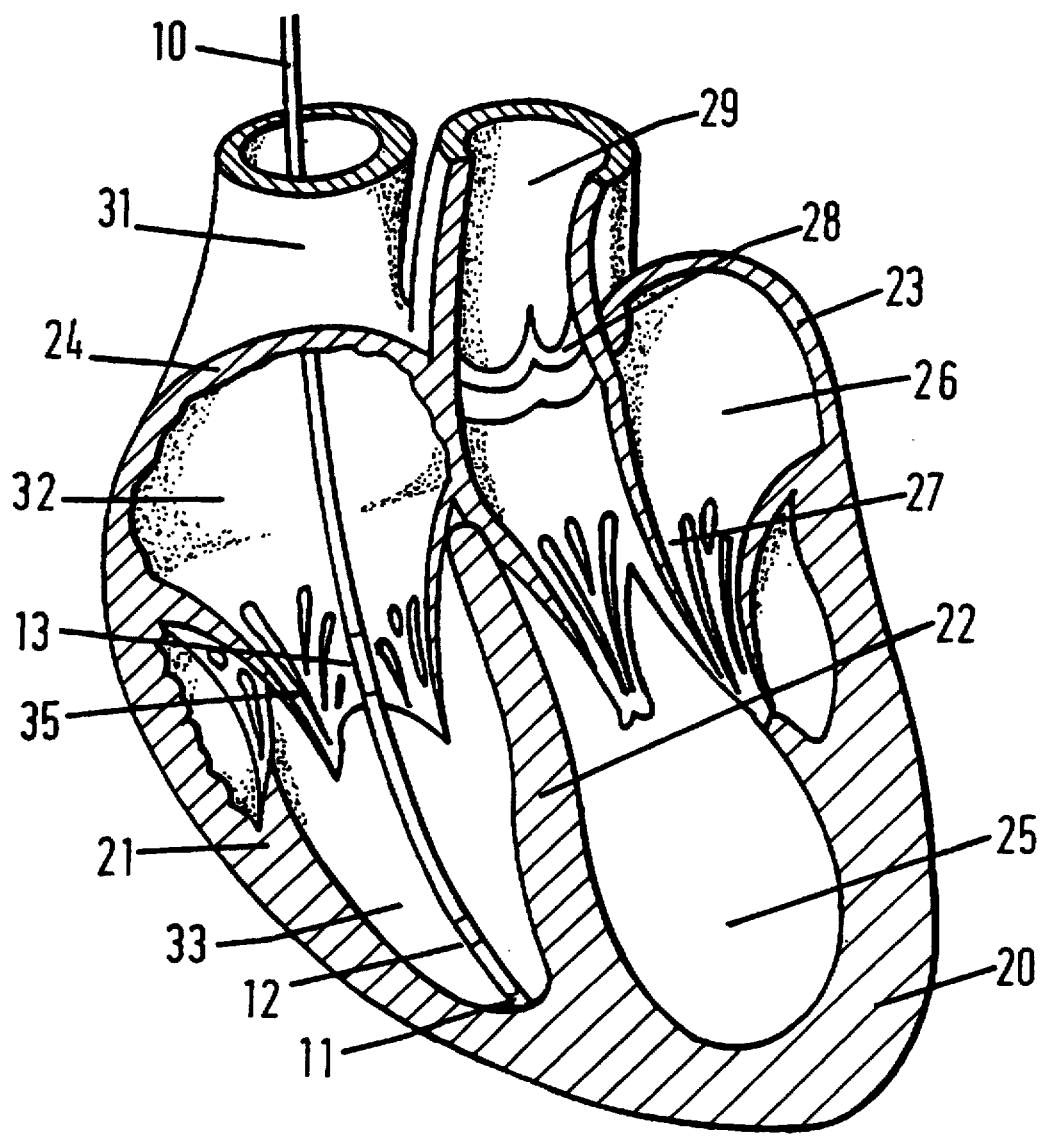
FIG. 2 shows the lead of FIG. 1 implanted in a human heart.

In the embodiment of FIG. 1, there is disclosed the distal end of a plastic lead body 10. Lead body comprises three electrodes 11, 12 and 13, one of them (13) being made of noble metal thus being a polarizable electrode. In the steady state of the ionic media, the positive DC voltage can be measured on the electrode 13 using the electrode 12 as a reference. Any other electrode within the electrolyte may be used as a reference electrode e.g. also the pacing electrode 11. If the flow of ionic media occurs, the concentration overvoltage occurs, and the voltage measured comprises a DC component being galvanic potential and an AC component being the consequence of flow variation. Moreover, any change of flow velocity causes the variation of the overvoltage. The overvoltage fluctuation is proportional to the magnitude of flow velocity variation. Electrodes 11 and 12 are used for cardiac pacing and for sensing of the ventricular potential.

In the embodiment of FIG. 2, there is disclosed a practical application of the pacemaker lead comprising the polarizable electrode in the vicinity of the tricuspid valve. The heart is disclosed in the four chamber cross-section view and the myocardial cross-section is visible of the left-ventricular wall 20, the right ventricular wall 21, the interventricular septum 22, the left-atrial wall 23 and the right-atrial wall 24. Two chambers of the left heart, left ventricle 25 and left atrium 26 are separated by the mitral valve 27. The left ventricular outflow tract consists of the aortic valve 28 and aorta 29. A cardiac pacing lead 10 is implanted through the vena cava superior 31 and the right atrium 32 in the right ventricle 33, with its active pacing electrode 11 located in the apex of the right ventricle. In the low right-atrial region, in the proximity of the tricuspid valve 35, the lead 10 comprises an additional electrode 13 made of the noble metal. Electrode 12 is an indifferent electrode and electrodes 11 and 12 are mounted adjacently to each other forming a bipolar pacing electrode system. The blood inflow from the right atrium 32 into the right ventricle 33 and through the tricuspid valve 35 causes the variation of the ions concentration in vicinity of the electrode 13. Accordingly, the overvoltage, measured between electrodes 13 and certain reference electrode within the human body occurs. Although the reference electrode is in this embodiment the electrode 12 which is located within the heart, the reference electrode could also be located in another part of the human body outside of the detecting area. The variation of said overvoltage represents the variation of blood flow. In this example, the bipolar pacing area is disclosed and therefore the pacing indifferent electrode 12 may be used as a reference electrode for overvoltage measurement. In an unipolar pacing system, the electrode 12 does not exist and the overvoltage may be measured between the electrode 13 and the pacemaker case (not shown).

FIG. 3 discloses a simplified electronic circuit of the single lead VDD pacemaker. The signal of the overvoltage sensing electrode 13, detected with reference to electrode 12 is transmitted via electrical conductors (not shown) to the proximal terminals 36 and 37, respectively of the lead and to the input of the AC filter-amplifier circuit 40. The filter has a bandpass freqency characteristic in order to amplify only the frequency spectrum of the AC voltage produced by the blood flow velocity variation, as well as to prevent the saturation by the galvanic DC potential. The signal of the bipolar pacing-sensing electrode 12/11 is led via terminals 37 and 34 to the input of the filter-amplifier circuit 41. The filter has a bandpass frequency characteristic in order to amplify only the frequency spectrum of the intracardiac ECG, as it is known in the art. Outputs of filter-amplifiers 40 and 41 are led to the input of data acquisition circuits 42 and 43 respectively and to a logic and control circuit 44 wherein the signal processing occurs. Filteramplifier 40 processes the signal of the concentration overvoltage superimposed with ventricular intracardiac electrogram. Filteramplifier 41 processes only the intracardiac electrogram signal. The output circuit 45 which is connected to terminals 37 and 34 is a pacing pulse generator. The logic and control circuit 44 generates the blanking period of both amplifiers during the pacing pulse release by a pulse generator 45, as it is described in prior art, in order to prevent the sensing of the pacing pulse voltage and consequent polarization voltage by amplifiers 40 and 41. Moreover, it generates a special sensing blanking period of only amplifier 40 during the sensing of an intracardiac electrogram by the amplifier 41 in such a way as to avoid the misinterpretation of an electrogram signal detected by the bipolar electrode 13/12 as a signal of the blood flow. The same kind of blanking period would be also useful in unipolar pacing system wherein the sensing of intracardiac EGM happens both between electrode 13 and pacemaker case as well between electrode 11 and pacemaker case.

In the embodiment of FIG. 4, there is disclosed the distal end of a plastic lead body 110. Lead body comprises two ring electrodes 111 and 112 made of different materials. Electrodes, when immersed within the ionic liquid media such as blood, constitute a galvanic cell producing galvanic voltage. In this particular example, the electrode 111 is an anode and the electrode 112 is a cathode. For example, the electrode 111 can be made of gold and the electrode 112 of stainless steel. Accordingly, in the steady state of the ionic media, the positive voltage can be measured on the electrode 111 using the electrode 112 as a reference. If the flow of ionic media occurs, the measured galvanic voltage increases. Moreover, any change of flow velocity causes the variation of the galvanic voltage. The increase of voltage is proportional to the flow velocity increase. There is an active pacing electrode 113 which normally, when implanted within the heart, has a contact with endocardium. Electrical conductors 114, 115 and 116 are used for electrical connection of electrodes 111, 112 and 113, respectively with the tripolar connector (not shown) at the proximal termination (not shown) of the lead.

Figure 5:
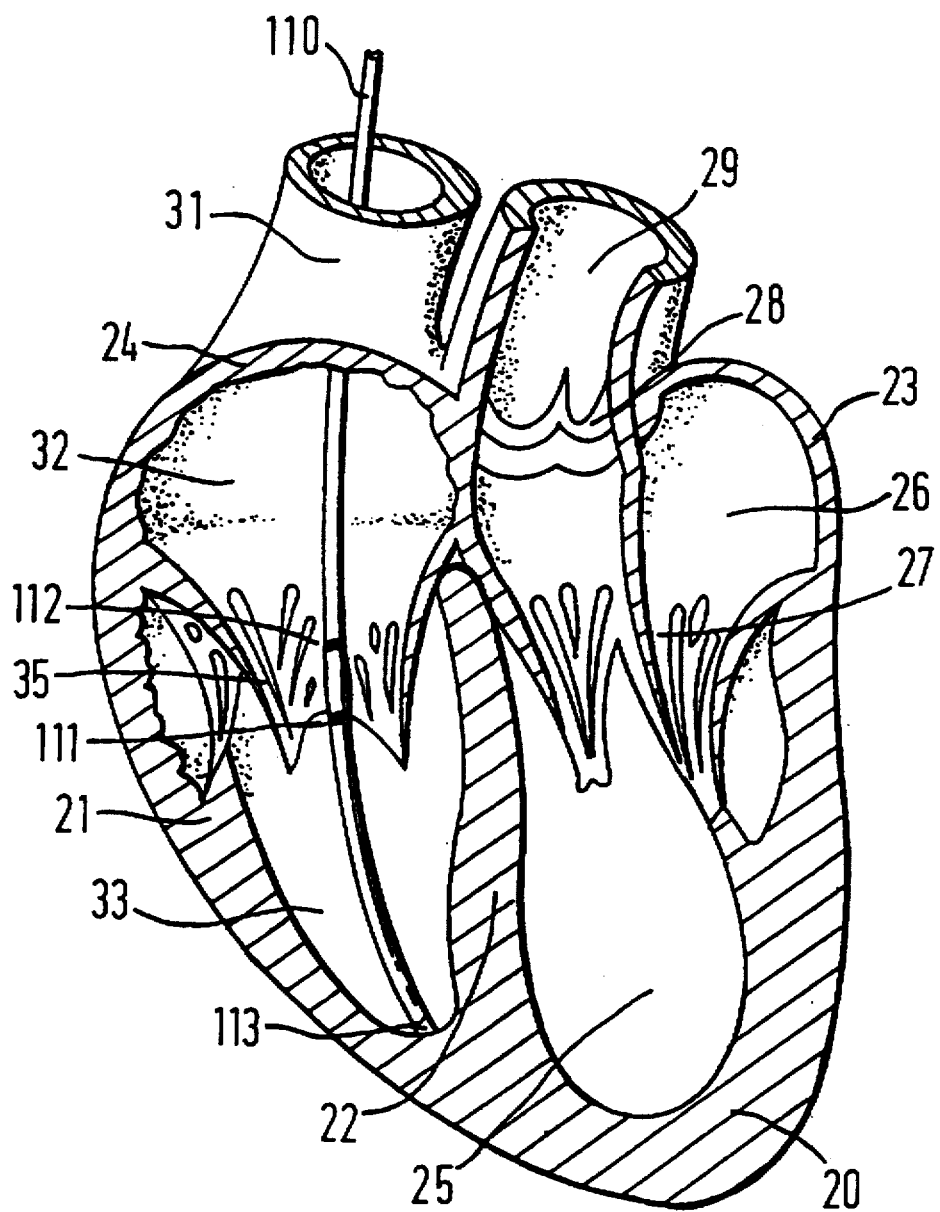
FIG. 5 shows the lead of FIG. 4 implanted in a human heart.

In the embodiment of FIG. 5, there is disclosed a practical application of the pacemaker lead comprising the electrodes forming the galvanic cell in the vicinity of the tricuspid valve. The heart is shown in the same way as in FIG. 2 and it is referred to the description of this figure. A cardiac pacing lead 110 is implanted through the vena cava superior 31 and the right atrium 32 in the right ventricle 33, with its pacing electrode 113 located in the apex of the right ventricle. In the low right-atrial region, in the proximity of the tricuspid valve 35, the lead 110 comprises a cathode 112 and an anode 111. Electrodes 112 and 111 form a galvanic cell within the blood stream. The blood inflow from the right atrium 32 into the right ventricle 33 and through the tricuspid valve 35 causes the variation of the ions concentration in the vicinity of electrodes 112 and 111. Accordingly, the galvanic voltage, measured between electrodes 111 and 112 changes. The variation of said voltage represents the variation of blood flow.

Figure 6:
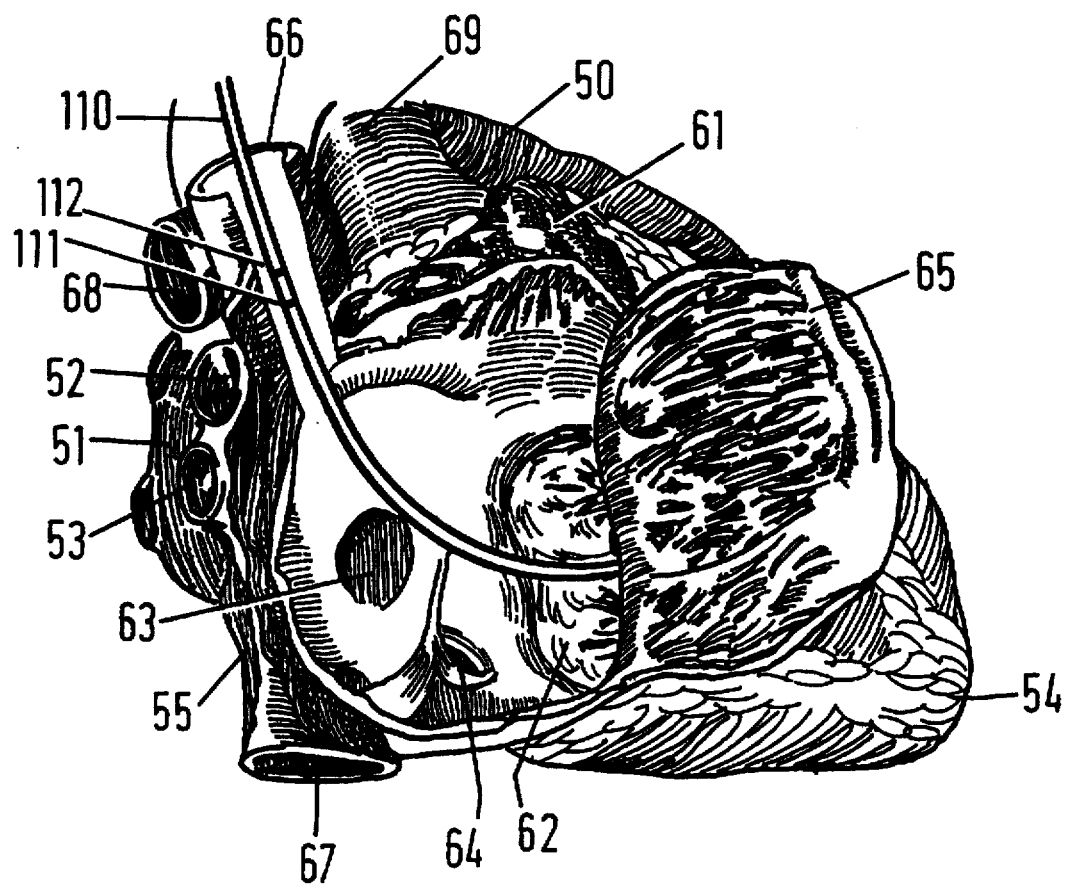
FIG. 6 shows another embodiment of a lead constructed in accordance with the principles of the present invention for flow measurement in the superior vena cava.

FIG. 6 shows the heart opened at the right trial appendage 61. There are tricuspid valve 62, fossa ovalis 63, coronary sinus valve 64 and crista terminalis 65 within the right atrium. The vena cava superior 66 and the vena cava inferior 67 as well as the pulmonary artery 68 and the aorta 69 with truncus pulmonalis 50 are disclosed. The left atrium 51 with right superior pulmonary vein 52 as well as with right inferior pulmonary vein 53 are shown. The right ventricular apex 54 is disclosed as well as the residue of the pericardium 55. The pacemaker lead 110 is implanted through the vena cava superior 66 and right atrial cavity through the tricuspid valve 62 in the right ventricle with its tip (not shown) in the area of apex 54. The lead 110 comprises a cathode 112 and an anode 111 which form a galvanic cell within the blood stream of the vena cava superior 66. The variation of galvanic voltage measured between anode 111 and cathode 112 represents the variation of blood flow within the vena cava superior.

In the embodiment of FIG. 7, there is disclosed the distal end of a plastic lead body 210. The lead body comprises three ring electrodes 211, 212 and 213, one of them (213) being made of different material than the other two. There is an active pacing electrode 214 which normally, when implanted within the heart, has a contact with endocardium. Electrodes 212 and 213, when immersed within the ionic liquid media such as blood constitute a galvanic cell producing galvanic voltage. In this particular example, the electrode 213 is an anode and the electrode 212 is a cathode. For example, the electrode 213 can be made of gold and the electrodes 211 and 212 of steel. Accordingly, in the steady state of the ionic media, the positive voltage can be measured on the electrode 213 using the electrode 212 as a reference. If the flow of ionic media occurs, the measured galvanic voltage changes. Moreover, any change of flow velocity causes the variation of the galvanic voltage. The voltage fluctuation is proportional to the magnitude of flow velocity variation. Moreover, there are two identical bipolar sensing electrodes, the first one consisting of electrodes 211 and 212 and the second one consisting of electrodes 212 and 213. The first bipolar electrode has the same volume sensitivity characteristics as the second bipolar electrode. If the interelectrode spacing of electrodes 211, 212 and 213 is small relatively to the distance between cardiac muscle mass producing the intracardiac electrogram and sensing electrodes, sensed intracardiac electrogram of both bipolar sensing electrodes is approximately equal. Electrical conductors, 215, 216, 217 and 218 are used for electrical connection of electrodes 211, 212, 213, and 214 respectively with the quadripolar connector (not shown) at the proximal termination (not shown) of the lead.

Figure 8:
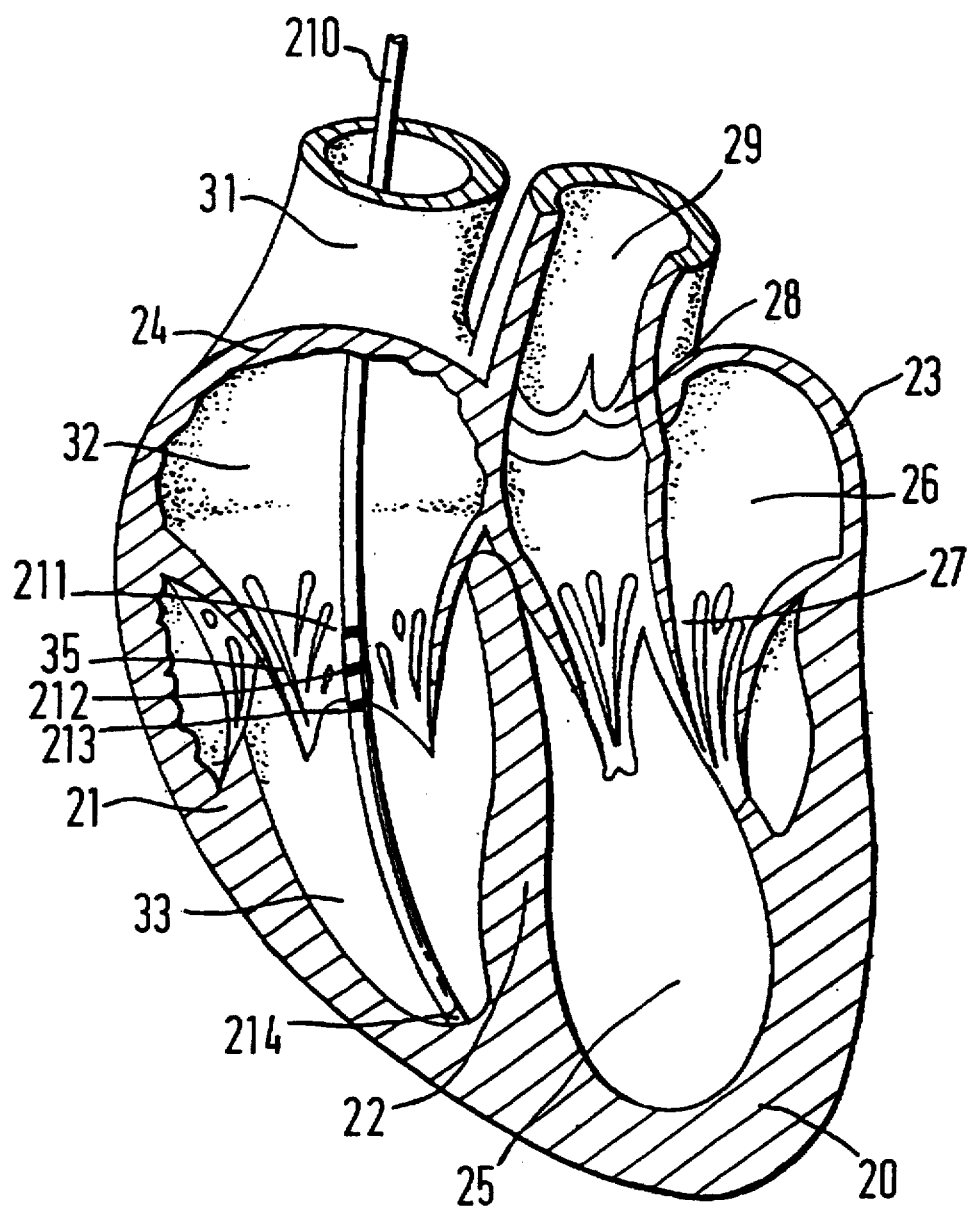
FIG. 8 shows the lead of FIG. 7 implanted in a human heart.

In the embodiment of FIG. 8, there is disclosed a practical application of the pacemaker lead comprising the electrodes forming the galvanic cell in the vicinity of the tricuspid valve. The heart is shown in the same way as in FIG. 2 and it is referred to the description of this figure. A cardiac pacing lead 210 is implanted through the vena cava superior 31 and the right atrium 32 in the right ventricle 33, with its pacing electrode 214 located in the apex of the right ventricle. In the low right-atrial region, in the proximity of the tricuspid valve 35, the lead 210 comprises a cathode 212 and an anode 213 and an additional electrode 211 made of the same material as cathode 212. Electrodes 211 and 212 are mounted adjacently to each other. Electrodes 212 and 213 form a galvanic cell within the blood stream. The blood inflow from the right atrium 32 into the right ventricle 33 and through the tricuspid valve 35 causes the variation of the ions concentration in the vicinity of electrodes 211, 212 and 213. Accordingly, the galvanic voltage, measured between electrodes 212 and 213 changes. The variation of said voltage represents the variation of blood flow. However, the electrodes 212 and 213 form also the bipolar sensing electrode and therefore they record the bipolar intracadiac electrogram produced by the cardiac muscle electric activity. The intracardiac electrogram signal appears to be a noise within the signal produced by the blood flow. Electrodes 211 and 212 constitute another bipolar sensing electrode. Because of the fact that these two electrodes (211 and 212) are made of the same material, they record only the intracardiac electrogram. If the interelectrode spacing of electrodes 211, 212 and 213 is small, the intracardiac electrogram recorded by first bipolar sensing electrode 211/212 will be approximately the same to the intracardiac electrogram recorded by second bipolar sensing electrode 212/213.

Figure 9:
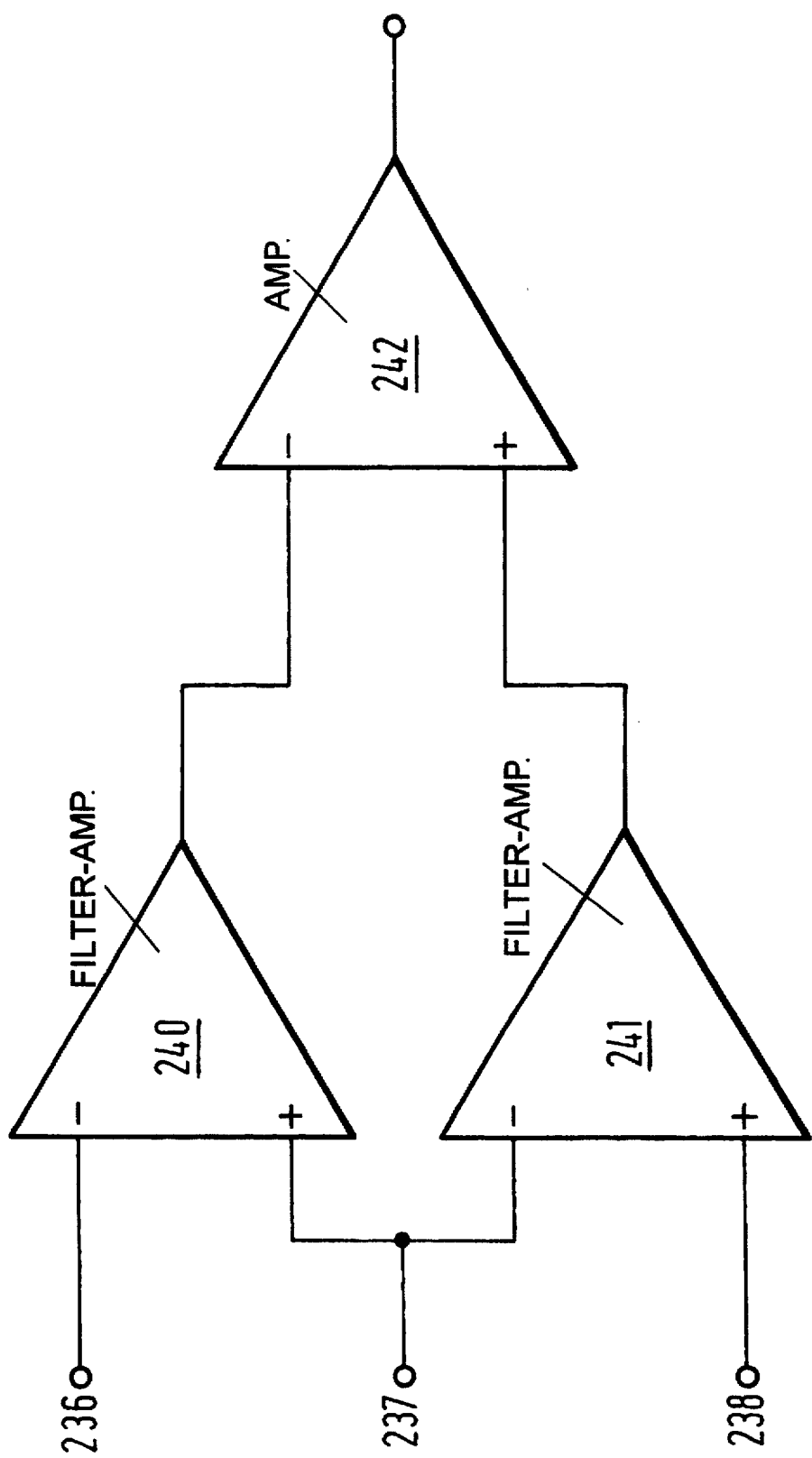
FIG. 9 is an electronic block circuit diagram for processing signals from the lead of FIG. 7.

FIG. 9 discloses a simplified electronic cicuitry of the signal processing. The signal of the bipolar sensing electrode 211/213 is led via therminals 236 and 237 to the input of the bandpass filter-amplifier circuit 240. The signal of the bipolar sensing electrode 212/213 is led via terminals 237 and 238 to the input of the another bandpass filter-amplifier circuit 241. Outputs of filter-amplifiers 240 and 241 are led to the input of a differential amplifier 242 wherein the signal of filter-amplifier 240 is subtracted from the signal of filter-amplifier 241. Filter-amplifier 240 processes the signal of the intracardiac electrogram and is accordingly adapted to frequency spectrum of the intracardiac EGM. Filter-amplifier 241 processes the superimposed signals, i.e. intracardiac electrogram and galvanic flow signal and is therefore adapted to the frequency spectra of both intracardiac EGM and flow signal. Accordingly, the signal at the output of the amplifier 242 represents the flow velocity characteristics. This is only the general principle, but it is obvious that those skilled in the art could design this circuit in a proper manner using analog to digital conversion and instead of the amplifier 242, utilising the microprocessor and appropriate software for signal subtraction. Algorithms for flow measurement calibration could be employed as well.

While specific embodiments of the present invention have been described, it should be understood that these embodiments are described for purpose of illustration only. The foregoing description is not intended in any way to limit the scope of the present invention. Rather is the intention that the scope of the invention be limited only as defined in the appended claims.

We claim:

1. An intracardiac blood flow velocity measurement system comprising:

a catheter adapted for insertion into a heart through a blood vessel;

at least one blood flow velocity detecting means, mounted on said catheter, for detecting blood flow velocity at a detecting position in a selected detecting area when said catheter is inserted into said heart;

a plurality of electrical conductors contained in said catheter, each conductor having a distal end electrically connected to said blood flow velocity detecting means and each conductor having a proximal end;

electronic circuitry means, connected to the respective proximal ends of said electrical conductors, for receiving and processing blood flow velocity data generated by said blood flow velocity detecting means; and said blood flow velocity detecting means comprising at least two electrodes respectively consisting of two different biocompatible materials, and at least a first of said at least two electrodes comprising a polarizable electrode and being disposed in said detecting position and a second of said at least two electrodes being disposed on said catheter axially spaced from said first electrode.

2. A system as claimed in claim 1 wherein said second electrode comprises a non-polarizable electrode.

3. A system as claimed in claim 2 wherein said non-polarizable electrode is mounted on said catheter at a position at which the blood flow velocity is less than blood flow velocity in said selected detecting area when said catheter is inserted into said heart.

4. A system as claimed in claim 1 wherein said second electrode comprises a polarizable electrode, and wherein said second electrode is mounted on said catheter at a position within said selected detecting area when said catheter is inserted into said heart.

5. A system as claimed in claim 1 further comprising a third electrode mounted on said catheter and connected to the distal end of one of said electrical conductors, said third electrode and said second electrode, in combination, comprising means for measuring an intracardiac electrocardiogram.

6. A system as claimed in claim 1 comprising a pacing electrode disposed at a distal end of said catheter and connected to one of said electrical conductors, and wherein said electronic circuitry means comprises means for generating a pacing control signal, dependent on said blood flow velocity data, and for supplying a pacing signal to said pacing electrode for pacing said heart dependent on said control signal.

7. A system as claimed in claim 6 wherein said pacing electrode comprises said second electrode.

8. A system as claimed in claim 6 wherein said at least two electrodes, in combination, generate an electrical signal containing said blood flow velocity data, and wherein said electronic circuitry means include filter means for extracting said blood flow velocity data from said electrical signal for use by said means for generating a control signal.

9. A system as claimed in claim 1 wherein said detecting area comprises an area of said heart in which the tricuspid valve is disposed.

10. A system as claimed in claim 1 wherein said detecting area comprises a cavity of the superior vena cava.

11. A system as claimed in claim 1 comprising a pacing electrode disposed at a distal end of said catheter and connected to one of said electrical conductors, and wherein said electronic circuitry means comprises means for generating a pacing control signal, dependent on said blood flow velocity data, and for supplying a pacing signal to said pacing electrode for pacing said heart dependent on said control signal, and wherein said second electrode comprises a polarizable electrode disposed within said selected detecting area when said catheter is inserted into the heart, and said first and second electrodes, in combination, forming a galvanic cell within the blood whose blood flow velocity is to be measured, and wherein said electrical conductors contained in said catheter comprise first and second electrical conductors respectively connected to said first and second electrodes, and a third electrical conductor connected to said pacing electrode.

12. A system as claimed in claim 11 wherein said galvanic cell formed by said first and second electrodes generates a galvanic voltage which varies throughout a cardiac cycle of said heart, and wherein said electronic circuitry means comprises means for evaluating said galvanic voltage as said blood flow velocity data.

13. A system as claimed in claim 12 wherein said first electrode is mounted on said catheter closer to said distal end of said catheter than said second electrode, said first electrode comprising an anode of said galvanic cell and said second electrode comprising a cathode of said galvanic cell, and wherein said galvanic voltage is positive at said anode relative to said cathode, said galvanic voltage thereby indicating a flow direction of said blood flow velocity from the cathode to the anode of said galvanic cell when said catheter is inserted into said heart.

14. A system as claimed in claim 13 wherein said detecting area comprises an area of said heart in which the tricuspid valve is disposed, and wherein said galvanic voltage includes a first peak indicative of diastolic filling caused by a ventricular relaxation in said heart and a second peak indicating an atrial filling caused by an atrial contraction in said heart, and wherein said electronic circuitry means comprises means for detecting said first and second peaks.

15. A system as claimed in claim 13 wherein said detecting area comprises a cavity of the superior vena cava, and wherein said galvanic voltage includes a first peak indicative of diastolic filling caused by a ventricular relaxation in said heart and a second peak indicating an atrial filling caused by an atrial contraction in said heart, and wherein said electronic circuitry means comprises means for detecting said first and second peaks.

16. A system as claimed in claim 11 further comprising a third electrode, said third electrode and one of said first and second electrodes comprising, in combination, bipolar sensing means for detecting a bipolar intracardiac electrocardiogram produced by cardiac muscle electrical activity, and wherein said electronic circuitry means comprises means for processing said intracardiac electrocardiogram, in combination with said galvanic voltage, for producing a signal indicative of said blood flow velocity.

17. A system as claimed in claim 16 wherein said first, second and third electrodes comprise a first pair of adjacent electrodes and a second pair of adjacent electrodes, the electrodes in said first pair of electrodes consisting of different material and the electrodes of said second pair of adjacent electrodes consisting of the same material.

18. A system as claimed in claim 17 wherein said second pair of adjacent electrodes comprise said galvanic cell, and wherein said second pair of adjacent electrodes detect said intracardiac electrocardiogram.

19. A system as claimed in claim 16 wherein said means for processing said galvanic voltage and said intracardiac electrocardiogram in combination comprise means for subtraction said intracardiac electrocardiogram from said galvanic voltage for producing said signal indicative of blood flow which is free of said cardiac muscle electrical activity.

20. A system as claimed in claim 16 wherein said electronic circuitry means include means for measuring an over-voltage at said first electrode and wherein said control means comprise means for controlling pacing of said heart dependent on said over-voltage.

21. A system as claimed in claim 20 wherein said electronic circuitry means comprise means for generating a blanking period for said means for measuring an over-voltage, dependent on said intracardiac electrocardiogram.

22. A system as claimed in claim 1 wherein said first electrode consists of a noble metal.

* * * * *